United States Patent [19]

Siegel et al.

[11] Patent Number: 4,720,191

[45] Date of Patent: Jan. 19, 1988

[54] METHOD AND APPARATUS FOR LIGHT SPAN MICROSCOPIC DARK-FIELD DISPLAY OF OBJECTS

[75] Inventors: Augustin Siegel, Oberkochen; Peter Seidel, Steinheim, both of Fed. Rep. of Germany

[73] Assignee: Carl-Zeiss-Stiftung, Heidenheim/Brenz, Fed. Rep. of Germany

[21] Appl. No.: 931,763

[22] Filed: Nov. 17, 1986

[30] Foreign Application Priority Data

Nov. 19, 1985 [DE] Fed. Rep. of Germany ........ 3540916

[51] Int. Cl.⁴ ............................................. G01N 21/47
[52] U.S. Cl. ..................................... 356/237; 250/563
[58] Field of Search ................ 356/222, 237, 239, 337, 356/340; 250/562, 563, 572

[56] References Cited

U.S. PATENT DOCUMENTS 4,595,289  6/1986  Feldman et al. ..................... 356/237
4,601,577  7/1986  Gotou et al. ......................... 356/237

Primary Examiner—Eugene R. LaRoche
Assistant Examiner—Robert J. Pascal
Attorney, Agent, or Firm—Stonebraker, Shepard & Stephens

[57] ABSTRACT

A method used for the inspection of semiconductor structures under a light scan microscope which scans the surface of the wafer or other specimen (12) with a beam of light which is focused in spot form by the objective (18). In order to produce a dark-field image in which the linear semiconductor structures of the wafer are suppressed and only defects and particles of dirt are visible, the signals of four detectors (10a–10d) arranged outside the illuminating aperture of the objective within the channel of the dark-field ring condenser (6) are subjected to a logical "and" operation.

11 Claims, 7 Drawing Figures

Fig. 6
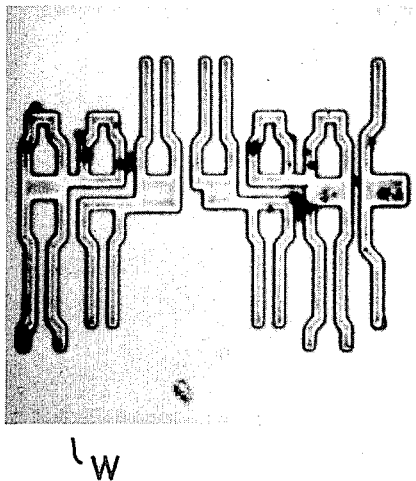
$L_W$
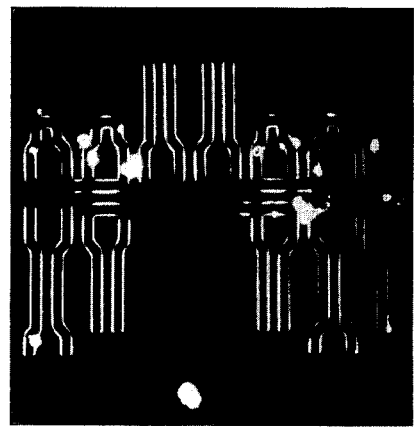
$L_V$
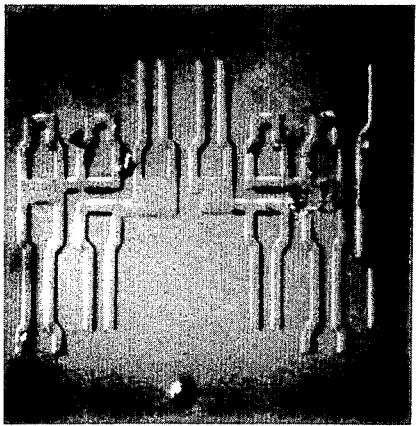
$L_X$
$L_Y$

METHOD AND APPARATUS FOR LIGHT SPAN MICROSCOPIC DARK-FIELD DISPLAY OF OBJECTS

BACKGROUND OF THE INVENTION

Dark-field contrasting methods are being increasingly employed for the microscopic inspection of semiconductor substrates, since such methods permit better recognition and measurement, for instance, of the line widths of the microstructures on the substrates than is possible with bright-field observation. For this purpose, conventiona microscopes are provided with special objectives around which is placed a so-called dark-field condenser in the form of an annular mirror. This annular mirror focuses onto the object an illuminating light beam which is conducted concentrically around the objective and illuminates the entire image field.

It is also known in the art to use what are called light scan microscopes in order to inspect semiconductor substrates. These instruments, known in part also as laser scan microscopes (LSM), produce a light spot which is generally diffraction-limited and which is moved line-by-line over the object by means of deflectin mirrors. In these microscopes, the objective serves to focus the scanning light beam on the object.

In order to produce a dark-field image with such microscopes, there is used the signal of a detector which is arranged alongside the objective and therefore outside the aperture of the illuminating optical system. Such a light scan microscope is disclosed, for instance, in U.S. Pat. No. 4,441,124 of Heebner et al., granted Apr. 3, 1984, in which the entire light detected by the dark-field condenser (annular mirror) is fed to a single detector, which supplies the dark-field signal. The dark-field images thus obtained are, however, not optimal with respect to ease of recognition of the line structure extending in two pronounced preferred directions on the semiconductor substrate. In particular, it is not readily possible to bring out defects or particles of dirt on the surface of the substrate clearly against the structures applied.

U.S. Pat. No. 4,460,273 of Koizumi et al., granted July 17, 1984, shows a light scan microscope containing two dark-field detectors arranged alongside the objective, the line between them extending perpendicular to the line structures on the substrate surface, as illustrated in FIGS. 16 and 17 of this patent. With such an arrangement, it is possible to suppress effevively only structures having a single preferred direction. Thus unambiguous discrimination between structure and defect is not possible. Furthermore, the detector arrangement must always be directed at right angles to the structures on the substrate, making the operation or use of the instrument difficult.

European Pat. No. 0,011,709 of Wagner, published June 23, 1982, describes a microscope for inspection of semiconductors, the objective of which contains a plurality of light guides arranged in the rear focal plane of the objective itself. These light guides can be combined in sector form, and conduct light to one or more detectors.

The effective aperture of the objective is limited by such an arrangement in the manner that the diffraction-limited focusing of the illuminating light conducted over the objective which is required in light scan microscopes is no longer assured, i.e., the resolving power is impaired. Furthermore, it is difficult to integrate a larger bundle of light-guide fibers into the objective without detriment to the ease of handling, as in interchange, or application to a turret. That European patent does not specifically indicate the manner in which the signals of several detectors are to be processed in order, for instance, to emphasize defects or particles of dirt in the dark-field image.

The object of the present invention is to provide a method of inspecting incident-light objects such, for example, as wafers in the semiconductor industry, which assures the best possible recognition of defects, impurities, etc., and to provide apparatus suitable for this purpose which may be constructed without great expense by a substantial use of standardized components already available.

This object is achieved in the manner set forth in the claims.

The invention makes use of the fact that particles of dirt such as dust, defects, and, for instance, torn edges on semiconductor structures disperse light without any pronounced preferred direction, while the scattering characteristic curve of well-defined smooth edges and surfaces has a pronounced preferred direction. Therefore, if at least three and preferably four or more detectors are arranged in a circle around the objective (or around the condenser, in the case of substage illumination), and if these condensers simultaneously supply signals of comparable size, this constitutes an indication of scattering caused by particles of dust or defects. The signal of all detectors resulting from a logical "and" operation therefore supplies an image of the object in which all structures having smooth edges are suppressed, regardless of the orientation of the edges. Automatic inspection of masks and wafers for dust and defects is thus substantially facilitated.

When four detectors are used, the signals of opposite detectors can furthermore be subtracted from each other and the sum of the two different signals can be used to display the image. It is thus possible to produce another dark-field image containing different information with the same detectors used to recognize impurities. In this other image, object structures such as lines and conductive paths are displayed three-dimensionally (pseudo-3D) and thus it is possible to make a decision as to whether a structure of an object is elevated or depressed (recessed).

Light scan microscopes usually also have, in any event, a bright-field detector, for instance in the form of a multiplier. It is advisable to superimpose the signal from this detector on the signal produced by the logical "and" operation in the manner of a false-color display. Particles of dust and defects then appeaar clearly emphasized in the bright-field image of the specimen, so that a simple association in space between the structure and the defects is possible.

In the apparatus of the present invention, a traditional dark-field objective is used for reflected-light displays. In the annular illumination channel surrounding the lens, which is not necessary for illumination purposes when used as a light scan microscope, three or more detectors are installed.

For the display of transparent objects such as, e.g., masks in transmitted light, the detectors are arranged in a suitable manner around the condenser of the microscope optical system, or are fastened to it.

An optical system which collects light separately for each detector is preferably arranged in front of the detectors. This makes it possible to keep the detector surface and thus the capacitance of the detector diodes small, so that the highest possible scanning frequency up to well into the megacycle region can be obtained with minimum detector noise.

Also it is advantageous for the electronic circuit to contain a comparator for the logical operation of the detector signals in each signal channel, i.e., in the signal path in front of the logic circuit. In such case it is possible, by suitable adjustment of the comparator threshold, so suppress dust or defects below a certain size in the image, if this is desired.

Further advantageous embodiments of the invention will be apparent from the following description read in conjunction with the drawings.

BRIEF DESCRIPTION OF THE DRAWINGS

In the accompanying drawings, illustrating preferred embodiments of the invention:

FIG. 4b is a vertical section taken diametrically on the line IVb—IVb of FIG. 4a;

FIG. 6 shows four pictures produced by the microscope of FIGS. 1-5 by different contrasting processes.

DESCRIPTION OF THE PREFERRED EMBODIMENTS

Figure 1:
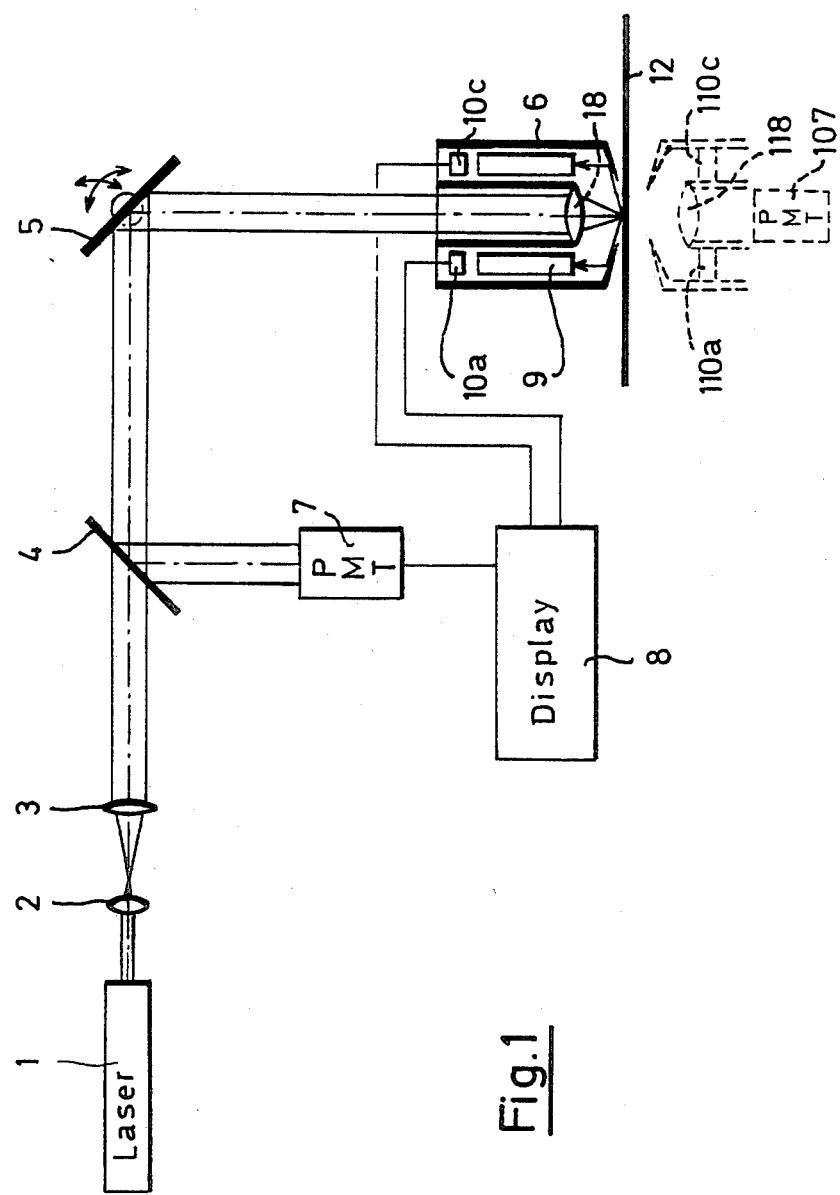
FIG. 1 is a basic diagram of a dark-field light scan microscope in accordance with the invention.

The light scan microscope shown in simplified schematic or diagrammatic form in FIG. 1 contains, on the illumination side, a laser 1 whose beam is broadened by an optical system comprising two lenses 2 and 3. The beam falls on the deflection unit 5 which deflects the laser beam into the two directions x and y perpendicular to the axis of the beam. After reflection on the deflection unit 5, the beam is focused as a spot by an objective 18 onto the surface of the object 12, for instance a wafer, and scans a region corresponding to the field of view of the objective.

This light scan microscope actually contains also other components, not shown here, in the illumination ray path, such as, e.g., an optical system by which the deflection unit 5 is imaged into the principal plane of the objective 18. The optical construction of a light scan microscope is described in further detail, for instance, in Federal Republic of Germany Pat. No. 30 37 983 and the corresponding U.S. Pat. No. 4,407,008 of Schmidt et al., granted Sept. 27, 1983.

The objective is a so-called "HD" objective having a dark-field condenser 6 arranged concentrically around the objective lenses. Such objectives are sufficiently known from conventional dark-field microscopes.

Between the beam expander 2, 3 and the deflection unit 5 there is a beam splitter 4 which deflects the light reflected back from the object 12 in the bright field onto a photomultiplier 7. The output of this photomultiplier 7 is fed to an amplifier or display unit 8 which is synchronized with the scanning movement of the deflection unit 5 and supplies a bright-field image of the object 12.

The parts described above are those of a known light scan microscope such as described, for instance, also in the above mentioned U.S. Pat. No. 4,441,124 of Heebner et al., granted Apr. 3, 1984.

In accordance with the present invention, four pin diodes are arranged symmetrically in a circle around the objective 18. Two of these diodes at diametrically opposite locations are shown at 10a and 10c in FIGS. 1 and 2. The other two diodes, on a diameter at right angles to the diameter of the diodes 10a and 10c, would be designated as 10b and 10d, but they do not show in these views. All four diodes appear in the electronic wiring diagram of FIG. 5. The outputs of these diodes are connected to the display unit 8, as indicated in FIG. 1.

Figure 2:
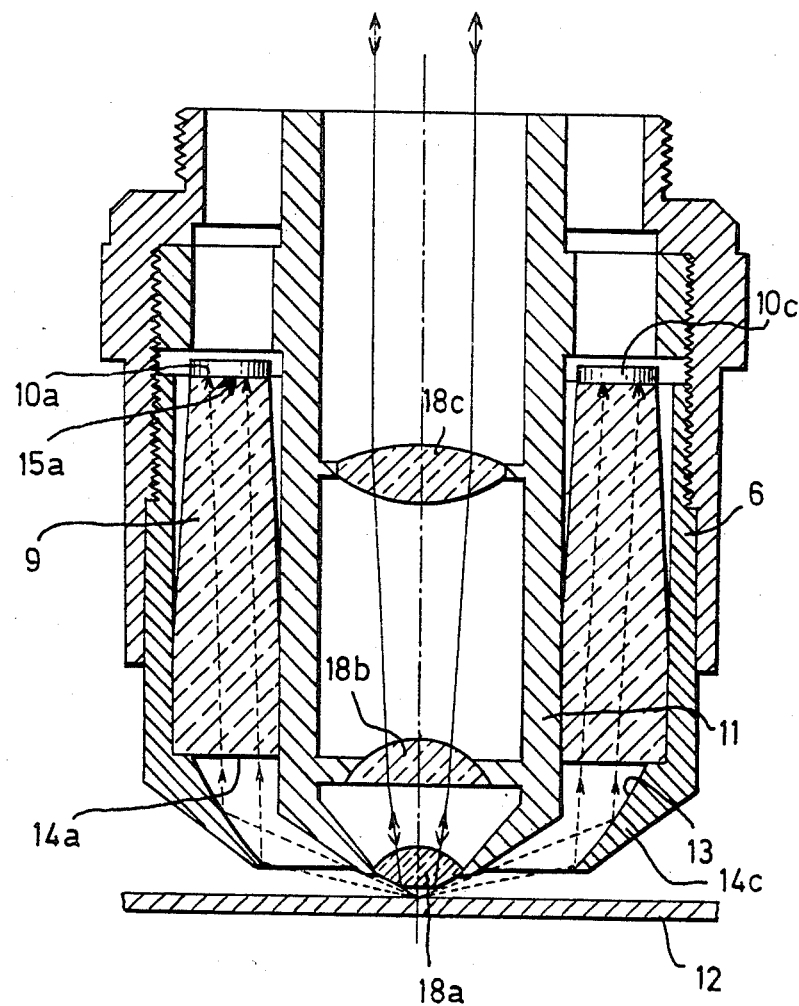
FIG. 2 is an axial diametrical section through the objective and associated parts of the microscope of FIG. 1.

As can be seen from the detailed showing in FIG. 2, these four diodes are located in the annular channel of the dark-field condenser 6 alongside the mount 11 for the three objective lenses 18a, 18b, and 18c. The dark-field condenser has an annular mirror 13. Above this annular mirror, between it and the four diodes, there is a light-collecting optical system indicated in general at 9, and shown separately and more clearly in FIG. 3.

Figure 3:
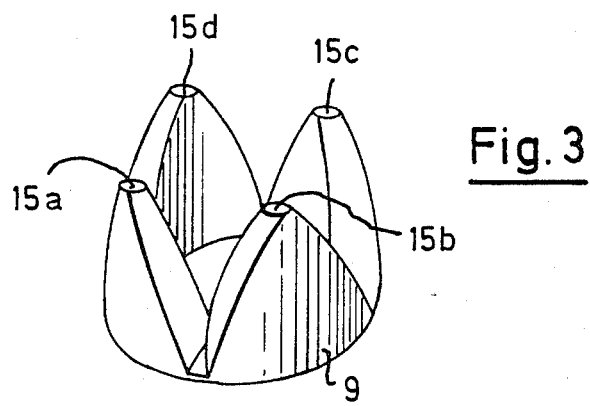
FIG. 3 is a perspective view of the collecting lens system forming a portion of FIGS. 1 and 2, with surrounding parts removed for clearer illustration.

This optical system has the shape which can be well understood from the perspective view in FIG. 3, formed of four conical frustums of transparent material such as glass or plastic, placed alongside of each other and on which the outside diameter of the mount 11 and the inside diameter of the dark-field condenser 6 have been developed. As a result of the shape shown in FIG. 3, the frustums having side edges tapering upwardly, each of the four frustums of the collecting lens system 9 concentrates the scattered light of one quadrant. The scattered light detected by one quadrant of the annular mirror 13 enters the bottom surface of the frustum (e.g., the surface 14a) as shown in dashed lines in FIG. 2, and as a result of total internal reflection all of the light entering this bottom surface (i.e., all of the stray light of one quadrant) is concentrated at the small top or end surface (e.g., 15a) of the particular frustum. The above mentioned detector (e.g., 10a) is placed there on the surface 15a. Therefore pin diodes or avalanche diodes having small light-sensitive surfaces can be arranged at this location. Such diodes have correspondingly small capacity, permitting high signal-processing frequencies with a minimum of noise.

Alternatively, it is possible to replace the total reflecting elements 9 by a collecting optical system consisting, for instance, of four lenses, or to impart to the annular mirror 13 the shape of four individual focusing mirrors. In the latter case, no further structural part for the collection of the light is necessary.

Figure 4A:
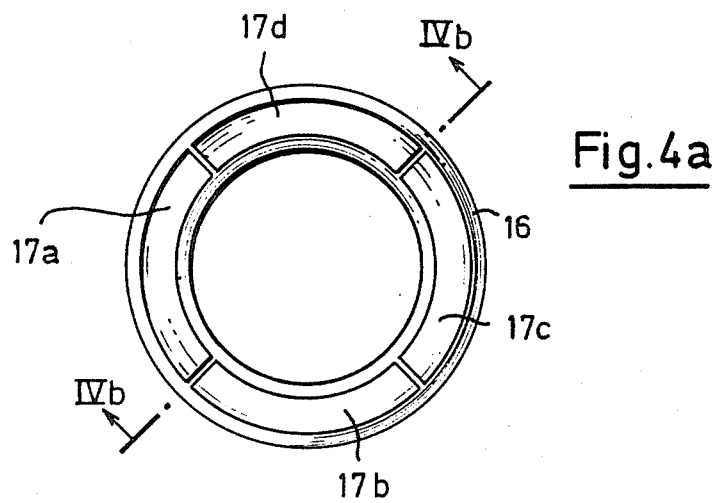
FIG. 4a is a top plan view of an alternative arrangement of diodes and collecting optical system.
Figure 4B:
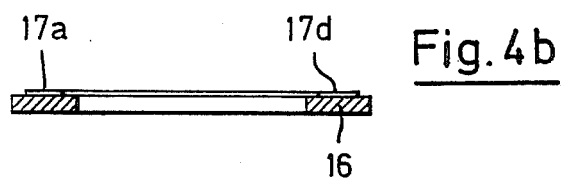

Another variant or alternative which may be used instead of the collecting optical system 9 with diodes 10a, 10b, etc., is the construction shown in FIGS. 4a and 4b. Here, there are four arcuate detector arrays 17a, 17b 17c, and 17d, each extending through a quadrant of the circle, applied on a circular support 16.

The structures illustrated in FIGS. 1 through 4b relate to the construction of light scan microscopes for reflected-light dark-field observation. It is apparent, however, that transmitted-light dark-field images of, for isntance, masks, can be produced in a similar manner. For this purpose, as shown in broken lines below the object 12 in FIG. 1, the detectors 110a–110c etc. (corresponding to the detectors 10a etc. previously described) are arranged around the condenser 118 or are fastened to it. Furthermore, the condenser 118 may be replaced interchangeably with a second objective of the same construction shown in FIG. 2, in order to permit either transmitted-light observation or reflected-light observation as required from time to time.

Figure 5:
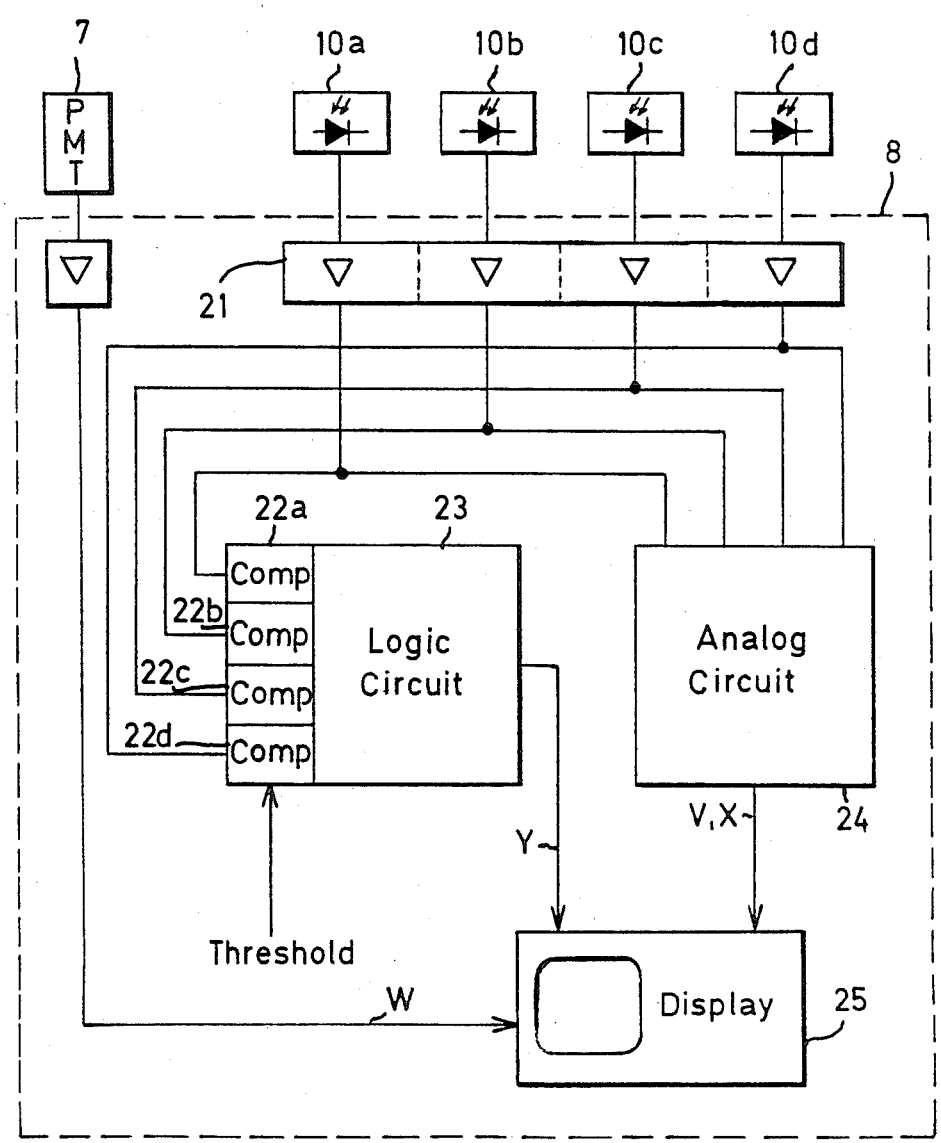
FIG. 5 is a basic diagram of the electronic system arranged behind and responsive to the dark-field detectors of FIGS. 1 and 2.

As indicated in FIG. 5, the signals from the respective diodes 10a–10d (or from the diodes 110a, etc., when such diodes are used) are amplified in a four-channel amplifier 21, and the respective outputs from this amplifier are fed both to a logic circuit 23 and to an analog circuit 24.

The analog circuit permits various switching possibilities. In a summation circuit, the signals of all four diodes (10a–10d or 110a–110d, as the case may be) are added. The resultant sum signal, which may be called the "V" signal, upon being synchronized with the scanning movement of the deflectin unit 5 in FIG. 1, gives at the display unit 25 a dark-field image such as shown, for example, at the upper right-hand image, labelled V, in FIG. 6. In this image, the edges of the semiconductor structures and particles of dust present on the surface of the wafer being observed appear bright against a dark background.

The analog circuit 24 (FIG. 5) also contains a circuit in which the signals of the two diodes which are arranged opposite each other in pairs (e.g., 10a and 10c as one pair, 10b and 10d as another pair) are subtracted in each case one from the other and the signal difference of one pair is then added to the signal difference of the other pair. The resulting signal may be called the "X" signal, and is the result of the logical operation expressed as $(a-c)+(b-d)=X$. This X signal when fed to the display unit 25 gives a pseudo-3D dark-field image of the semiconductor structure, as shown in the lower left-hand image of FIG. 6, labelled X. Elevations and depressions on the surface of the object can be very easily noted in this kind of image.

The logic circuit 23 (FIG. 5) contains a comparator section, having different comparators here labelled 22a, 22b, 22c, and 22d, respectively connected to the amplified outputs of the respective diodes 10a, 10b, etc. The thresholds of all of these comparators are jointly adjustable. The outputs of all of the comparators are connected together through an "and" gate which only gives off a signal when all four of the comparators pass simultaneously, that is, when all four diodes supply at the same time a signal having a given predetermined minimum value or intensity. The output of this logic circuit therefore only gives off a signal (which may be called the "Y" signal) when the scanning light beam focused on the specimen is scattered without pronounced preferred direction simultaneously in all four directions in space, this being the case upon impingement of the scanning beam on impurities, as already stated above. Therefore the Y siga when fed to the display unit 25, gives a display image in which the semiconductor structures are suppressed and only the defects and impurities appear bright on a dark background, as seen for example at the lower right-hand corner of FIG. 6, in the illustration labelled Y.

It has already been mentioned above, in connection with FIG. 1, that there is a photomultiplier 7 the output of which supplies a bright-field image of the object or specimen. This photomultiplier and its output, which may be called the "W" output or signal, are shown also in FIG. 5. In a very advantageous arrangement according to the invention, both the Y signal and the W signal are simultaneously fed to the monitor of the display unit 25 and are used for the display of different colors. There is then obtained a false color image which unfortunately can not be reproduced in the black and white drawings of a patent, but in which the defects and particles of dirt can be very simply and easily associated in space with the semiconductor structures. With this overlay of the Y image, in one color, on top of the W image, in another color, one can easily see exactly where, on the wafer or other specimen, each defect is located.

The individual parts or components of the electronic circuitry above mentioned, are well known in the art, so need not be further explained in detail, but they have not previously been combined or associated with each other and with the optical parts to produce the objects, improvements, and advantages of the present invention, so far as known at present.

What is claimed is:

1. A method for light scan microscopic dark-field display of objects which comprises providing a light scan microscope having an optical system including a member chosen from the group consisting of an objective and a condenser, said microscope having an illuminating optical system which has an aperture, arranging a plurality of at least three detectors in a circle around said member and outside said aperture of said illuminating optical system, and subjecting output signals from said detectors to a logical "and" operation in such manner that a dark-field image display (y) takes place only when all detectors simultaneously give an output signal of comparable size.

2. The method as defined in claim 1, wherein four detectors are used, arranged in two pairs with two detectors of each pair being substantially diametrically opposite each other, and wherein in each pair the signal from one detector is subtracted from the signal from the other detector to provide a difference signal, and the respective difference signals of the two pairs are added to provide a combined signal used for said image display.

3. The method as defined in claim 1, further comprising providing a bright-field detector, utilizing output signals from said bright-field detector to produce a bright-field image display (w), and superimposing said dark-field image display (y) and said bright-field image display (w) over each other in different colors.

4. Apparatus for light scan microscopic dark-field display of objects, said apparatus comprising a light scan microscope having an optical system including a member chosen from the group consisting of an objective and a condenser, a plurality of at least three detectors arranged in an annular dark-field channel surrounding said member, said detectors providing output signals responsive to light reaching the respective detectors, and electronic circuit means for processing said output signals from said detectors.

5. Apparatus as defined in claim 4, wherein there are four detectors arranged in two pairs, with the two detectors of each pair being substantially diametrically opposite each other.

6. Apparatus as defined in claim 4, further comprising means forming an optical system in front of said detectors for collecting light for each detector separately.

7. Apparatus as defined in claim 6, wherein said optical system for collecting light comprises a plurality of conical frustums of transparent material in which light is concentrated by total internal reflection.

8. Apparatus as defined in claim 6, wherein said optical system for collecting light comprises a plurality of lenses.

9. Apparatus as defined in claim 6, wherein said optical system for collecting light comprises a plurality of segments of an annular mirror.

10. Apparatus as defined in claim 4, wherein said electronic circuit means includes a separate comparator receiving said output signal from each separate detector.

11. Apparatus as defined in claim 10, wherein said electronic circuit means includes a logical "and" gate, and means feeding output signals from all of said comparators to said gate.

* * * * *